US011046764B2

(12) United States Patent
Estelles et al.

(10) Patent No.: US 11,046,764 B2
(45) Date of Patent: Jun. 29, 2021

(54) NATIVE HUMAN ANTIBODIES FOR IMMUNE CHECKPOINT MODULATION TARGETS TIM-3 AND B7-H3

(71) Applicant: Trellis Bioscience, LLC, Menlo Park, CA (US)

(72) Inventors: Angeles Estelles, Belmont, CA (US); Mikhail Gishizky, Napa, CA (US); Stefan Ryser, Menlo Park, CA (US); Lawrence M. Kauvar, San Francisco, CA (US)

(73) Assignee: Trellis Bioscience, LLC, Menlo Park, CA (US)

( * ) Notice: Subject to any disclaimer, the term of this patent is extended or adjusted under 35 U.S.C. 154(b) by 473 days.

(21) Appl. No.: 15/861,410

(22) Filed: Jan. 3, 2018

(65) Prior Publication Data

US 2018/0186880 A1 Jul. 5, 2018

Related U.S. Application Data

(60) Provisional application No. 62/441,910, filed on Jan. 3, 2017.

(51) Int. Cl.

| *C07K 16/00* | (2006.01) |
| *C07K 16/28* | (2006.01) |
| *C07K 16/30* | (2006.01) |
| *A61P 35/00* | (2006.01) |

(52) U.S. Cl.
CPC .......... *C07K 16/2803* (2013.01); *A61P 35/00* (2018.01); *C07K 16/30* (2013.01); *C07K 2317/24* (2013.01); *C07K 2317/31* (2013.01); *C07K 2317/54* (2013.01); *C07K 2317/55* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 2003/0232009 | A1 | 12/2003 | Babcook |
| 2006/0074229 | A1 | 4/2006 | Mueller-Hermelink |
| 2009/0311245 | A1 | 12/2009 | Devy |
| 2011/0209246 | A1 | 8/2011 | Kovalic |
| 2013/0266574 | A1 | 10/2013 | Sleeman |
| 2014/0099320 | A1 | 4/2014 | Throsby |
| 2015/0218274 | A1 | 8/2015 | Sabatos-Peyton |
| 2015/0274838 | A1 | 10/2015 | Johnson |

FOREIGN PATENT DOCUMENTS

| WO | 2006055638 | 5/2006 |
| WO | 2014160627 | 10/2014 |
| WO | 2016014434 | 1/2016 |
| WO | 2016068802 | 5/2016 |
| WO | 2016068803 | 5/2016 |
| WO | 2018129090 | 7/2018 |

OTHER PUBLICATIONS

Paul, Fundamental Immunology, 3rd Edition, 1993, pp. 292-295.*
Rudikoff et al, Proc. Natl. Acad. Sci. USA, 79(6): 1979-1983, Mar. 1982.*
Colman P. M., Research in Immunology, 145:33-36, 1994.*
Pascalis et al, Journal of Immunology, 2002, vol. 169, pp. 3076-3084.*
Vajdos et al., Journal of Molecular Biology, 2002, vol. 320, pp. 415-428.*
"Ig heavy chain V region (clone VERG7)—human (fragment)", Protein, (Jan. 21, 2000), Database accession No. PH1268, URL: NCBI, XP055514573.
"Uncharacterized protein {ECO:0000313|EMBL:BAG27512.1}", UniProtKB, (Jun. 10, 2008), Database accession No. B2GCY0, URL: UniProt, XP055514591.
"Uncharacterized protein {ECO:0000313|EMBL:KLU36401.1}", UniProtKB, (Oct. 14, 2015), Database accession No. A0A0J1GBW8, URL: UniProt, XP055514587.
Beerli, et al., "Isolation of human monoclonal antibodies by mammalian cell display", Proceedings of the National Academy of Sciences (PNAS), National Academy of Sciences, vol. 105, No. 38, Sep. 23, 2008, pp. 14336-14341.
Huang, Jinghe, et al., "Islolation of human monoclonal antibodies from peripheral blood B cells", Nature Protocols, vol. 8, No. 10, Sep. 12, 2013, pp. 1907-1915.
Qiu et al., "Identifying the Epitope Regions of Therapeutic Antibodies Based on Structure Descriptors", International Journal of Molecular Sciences, (Nov. 24, 2017), vol. 18, No. 12, XP055514561.
Ryser et al., "High affinity anti-TIM-3 and anti-KIR monoclonal antibodies cloned from healthy human individuals", PLoS One, (Jul. 19, 2017), vol. 12, No. 7, p. e0181464, XP055514568.
Scheid, Johannes F., et al., "Broad diversity of neutralizing antibodies isolated from memory B cells in HIV-infected individuals", Nature, vol. 458, No. 7238, Apr. 2, 2009, pp. 636-640.
Wiley, "Antibody Structure and Function", Mar. 16, 1998, URL: https://www.wiley.com/legacy/products/subject/life/elgert/CH04.pdf.

* cited by examiner

*Primary Examiner* — Mark Halvorson
(74) *Attorney, Agent, or Firm* — FisherBroyles, LLP; Victoria L. Boyd; Frank W. Leak

(57) ABSTRACT

Novel monoclonal antibodies directed against immune checkpoint modulator (ICM) proteins TIM-3 and B7-H3 are useful in treating cancer and immune system disorders.

8 Claims, No Drawings

Specification includes a Sequence Listing.

NATIVE HUMAN ANTIBODIES FOR IMMUNE CHECKPOINT MODULATION TARGETS TIM-3 AND B7-H3

CROSS-REFERENCE TO RELATED APPLICATION

This application claims priority to U.S. provisional application Ser. No. 62/441,910 filed 3 Jan. 2017, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 388512013600SeqList.txt, date recorded: Jan. 3, 2018, size: 10,552 bytes).

TECHNICAL FIELD

The present invention relates to antibody molecules that can directly bind immune checkpoint modulator (ICM) proteins and thus regulate the function of an individual's immune system. More specifically, it relates to human antibodies capable of promoting elimination of tumor cells by T lymphocytes (T cells), Natural Killer cells (NK cells) and myeloid cells by either reducing inhibitory signals or augmenting stimulatory signals emanating from two ICM proteins, T cell immunoglobulin and mucin domain 3 protein (TIM-3, CD366), and B7-H3 (CD276). In addition, B7-H3 has been shown to be overexpressed in many cancers, hence direct targeting of B7-H3 on the tumor cell can be used to eliminate the cancer. Further, the invention relates to pharmaceutical use of such agents as well as to methods of manufacturing such agents using transfected cell lines.

BACKGROUND ART

Over the past 20 years, discovery of antibody therapeutics for cancer has focused on proteins associated with tumor cells (also known as tumor-associated antigens—TAAs-). Several such anti-tumor antibody drugs have been commercialized, including those targeting VEGF, Her2, EGFR, and CD20. The need for an exogenous source of these antibodies arises from the high variability in the natural immune response to tumor associated antigens. This variability is due in part to tumor secretion of immunosuppressive factors. Over the past 5 years, a new class of cancer therapeutics has been developed clinically that act by stimulating the immune system, thereby improving the body's natural ability to fight cancer. This class of therapeutics is known as immune checkpoint modulators (ICM). So far, all of the drugs in this class have themselves been antibodies, including the approved drugs Yervoy™ (ipilimumab), Opdivo™ (nivolumab) and Keytruda™ (pembrolizumab) whose respective targets are CTLA-4, PD-1 and PD-L1. These ICM antibodies work by temporarily lifting a brake on the immune system thereby counteracting tumor induced immune suppression. The ICM drugs have proven to be particularly effective in treating melanoma, which frequently secretes immune suppressing factors.

Increased efficacy from combinations of these first generation ICM antibodies has been observed clinically, but accompanied by increased toxicity that resembles autoimmune disease. Further improvement thus depends on identifying combinations of agents that boost anti-tumor immunity while minimizing the adverse consequences of immune system stimulation. Native human antibodies with ICM activity are of particular interest in this regard, as they have been pre-selected naturally to be well tolerated. Such native antibodies may preferentially bind to particular ICM targets, or to particular epitopes on those targets. More than 20 potential ICM targets have been described in the scientific literature. Of particular interest for the present invention are antibody molecules that bind ICM proteins TIM-3 and B7-H3.

Alternatively, B7-H3 is an appropriate TAA for antibody targeted treatment since its expression is mainly restricted to the tumor, minimizing the risk of cytotoxicity in normal tissues. Of interest are B7-H3 antibodies that are able to mediate antibody-dependent cell-mediated cytotoxicity (ADCC). Also of interest are antibodies capable of being internalized in the cancer cells, making them candidates for Antibody Drug Conjugates (ADC) that can carry toxins or radioligands into the cell. Native human antibodies with anti-B7-H3 activity of either type are of particular value for minimizing off-target reactivity and rejection as a foreign protein.

U.S. Pat. No. 7,470,428 discloses the full length protein TIM-3 sequence ("Compositions and methods related to TIM-3, a Th1 specific cell surface molecule"). U.S. 2016/0257758 ("Antibody therapeutics that bind TIM3"); U.S. Pat. No. 8,552,156 ("Anti-TIM-3 Antibody"); U.S. 2015/218274 ("Antibody molecules to TIM-3 and uses thereof"); U.S. 2016/0257749 ("Anti-TIM3 antibodies and methods of use") and U.S. 2015/0086574 disclose "Antibodies binding to the Extracellular Domain (ECD) of TIM3". The antibodies disclosed below, derived from the natural human immune repertoire, and produced recombinantly are distinct compositions from these antibodies.

U.S. Pat. 2002/0198143 discloses the full length protein B7-H3 sequence ("B7-Like Polynucleotides, Polypeptides and Antibodies"). U.S. 2013/0078234 ("Anti B7-H3 Antibody") and U.S. Pat. No. 8,802,091 ("Antibodies reactive with B7-H3 and uses thereof") disclose Antibodies binding to the Extracellular Domain (ECD) of B7-H3. The antibodies disclosed below, derived from the natural human immune repertoire, and produced recombinantly are distinct compositions from these antibodies.

DISCLOSURE OF THE INVENTION

To generate therapeutic antibodies against the broad class of candidate ICM targets, we have used our previously described CellSpot technology for identifying rare antibodies (defined by specificity and affinity) within the memory B-cell compartment of the human immune system. Native human antibodies against several ICM targets have been recovered by this means. Surprisingly these antibodies have been cloned from healthy blood donors with no known cancer. In other words, the pharmacological approach represented by administration of ICM antibodies appears to have a natural counterpart, consistent with the long standing immune surveillance concept that in healthy individuals incipient tumors are eliminated by the immune system. The low frequency of memory B cells making high affinity antibodies to ICM targets further suggests that the natural ICM mechanism is transient, leaving a footprint in the memory B cell repertoire without leading to long term autoimmune disease. Here we describe antibody molecules that selectively bind to either TIM-3 or B7-H3 with high affinity and specificity. These antibody molecules can be used (alone or in combination with other agents or therapeutic modalities) to treat, prevent and/or diagnose cancer, immune disorders, infectious disease, Crohn's disease, sepsis and other immune system related health diseases.

TIM-3 is a transmembrane glycoprotein that is expressed on T cells (Monney, L., et al., *Nature* (2002) 415:536-541) as well as phagocytic cells such as macrophages and dendritic cells (Chiba, S., et al., *Nat. Immunol.* (2012) 13:832-842). TIM-3 is believed to be a negative regulator of T cell responses. For example, binding of TIM-3 to its putative ligand, galectin-9, on Th1 cells, results in Th1 cell death. Further, blockade of TIM-3 increases IFN-γ secreting T cells (Zhu, C., et al., *Nat. Immunol.* (2005) 6:1245-1252). Additionally, co-blockade of TIM-3 and another of its putative ligands, CEACAM1, leads to enhancement of anti-tumor immune responses with improved elimination of tumors in mouse colorectal cancer models (Huang, Y. H., et al., *Nature* (2015) 517:386-390). Microarray analysis of hematopoietic stem cells from acute myeloid leukemia (AML) patients and normal hematopoietic stem cells revealed that TIM-3 is expressed on AML stem cells. This analysis suggests the possible involvement of TIM-3 in hematological malignancy (Majeti, R., et al., *Proc. Natl. Acad. Sci.* (2009) 106:3396-3401).

B7-H3 is a transmembrane glycoprotein belonging to the "B7-CD28" immunoregulatory superfamily with two immunoglobulin-V-like and two immunoglobulin-C-like domains (e.g., IgV-IgC; Steinberger, P., et al., *J Immunol.* (2004) 172:2352-9). Other members of this family include inducible co-stimulator ligand (ICOS-L), the programmed death-1 ligand (PD-L1) and, the programmed death-2 ligand (PD-L2) (Collins M., et al., Genome Biol. (2005) 6:223). B7-H3 protein expression is tightly regulated in healthy individuals and is not expressed on resting B or T cells, monocytes, or dendritic cells. However, B7-H3 is induced on dendritic cells by IFN-γ and on monocytes by GM-CSF (Sharpe, A. H. and Freeman, G. J. Nat Rev Immunol (2002) 2:116-26) and is believed to inhibit Th1, Th2, or Th17 cells in vivo (Prasad, D. V., et al., J Immunol (2004) 173:2500-2506 and Yi, K. H. and Chen, L. Immunol Rev (2009) 229:145-151). Increased expression of B7-H3 on tumor cells is associated with increased severity of disease and poorer clinical outcomes (Zang, X., et al., *Mod. Pathol.* (2010) 23:1104-1112), suggesting that B7-H3 is exploited by tumors as an immune evasion pathway (Hofmeyer, K. A. et al., *Proc. Natl. Acad. Sci. USA*. (2008) 105:10277-8; Picarda, E. et al., Clin Cancer Res (2016) 22:3425-31). Furthermore, B7-H3 has been shown to be upregulated in many types of cancers (while no presence was found in surrounding healthy tissues) such as: breast cancer (Arigami, T., et al., *Ann. Surg.* (2010) 252:1044-1051); neuroblastoma (Castriconi, R., et al., *Proc. Natl. Acad. Sci. USA*. (2004) 101:12640-12645; Kramer, K., et al., J. Neurooncol. (2010) 97:409-418); melanoma (Wang, J., et al., *J. Invest Dermatol.* (2013) 133:2050-2058); gastric carcinoma (Wu, C. P., et al., *World J. Gastroenterol.* (2006) 12:457-459); pancreatic cancer (Yamato, I., et al., *Br. J. Cancer*. (2009) 101:1709-1716) and ovarian carcinoma (Zang, supra 2010). Direct target of B7-H3 alone or conjugated with a toxin or radioligand can be of interest in this regard.

MODES OF CARRYING OUT THE INVENTION

Human antibodies such as those disclosed here are particularly favorable from both an efficacy perspective (having been cloned from healthy donors) and a safety perspective (reduced chance of off-target reactivity that would create toxicity). The frequency of human antibodies to a particular target in the natural human repertoire is typically orders of magnitude lower than in the repertoire of immunized mice. Accordingly, a high throughput technology capable of surveying millions of individual antibody producing human B lymphocytes is needed. Since human B cells have a very limited lifetime ex vivo (under 10 days), the technology must also operate within that time window.

To accomplish the survey and recovery of rare favorable cells, we used the previously described CellSpot™ technology (U.S. Pat. Nos. 7,413,868 and 7,939,344, incorporated herein by reference). This assay method effectively shrinks an ELISA equivalent assay down to a virtual well of nearly single cell dimensions by capturing secreted IgG from a single cell as a footprint in the vicinity of the cell. In that way, 5 million B cells can be readily analyzed. Further, by use of microscopic multiplexing reagents (combinatorially colored fluorescent latex microspheres, cf U.S. Pat. No. 6,642,062, incorporated herein by reference), each clone's secreted antibody footprint can be characterized in detail for specificity and/or affinity using multiple biochemical probes. The fidelity of the quantitative assay is sufficient to enable rescue of extremely rare favorable cells from the survey population. The cloned antibody encoding genes expressed in an exogenous cell typically show a phenotype consistent with the original identifying assay.

The fully human antibodies of the invention are distinct from those found in nature, as they are prepared recombinantly. For complete antibodies, this includes constructing nucleic acids that encode a generic form of the constant region of heavy and/or light chain and further encode heterologous variable regions that are representative of human antibodies. Moreover, because the B cells are cultured prior to assay, mutations may arise during this ex vivo period.

As used herein, the term "antibody" includes immunoreactive fragments of traditional antibodies and their various fragmented forms that still retain immunospecificity such as Fab, F(ab')$_2$, F$_v$ fragments, single-chain antibodies in which the variable regions of heavy and light chain are directly bound without some or all of the constant regions. Also included are bispecific antibodies which contain a heavy and light chain pair derived from one antibody source and a heavy and light chain pair derived from a different antibody source. Similarly, since light chains are often interchangeable without destroying specificity, antibodies composed of a heavy chain variable region that determines the specificity of the antibody combined with a heterologous light chain variable region are included within the scope of the invention. Chimeric antibodies with constant and variable regions derived, for example, from different species are also included.

For the variable regions of mAbs, as is well known, the critical amino acid sequences are the CDR sequences arranged on a framework which framework can vary without necessarily affecting specificity or decreasing affinity to an unacceptable level. Definition of these CDR regions is accomplished by art-known methods. Specifically, the most commonly used method for identifying the relevant CDR regions is that of Kabat as disclosed in Wu, T. T., et al., *J. Exp. Med.* (1970) 132:211-250 and in the book Kabat, E. A., et al. (1983) *Sequence of Proteins of Immunological Interest*, Bethesda National Institute of Health, 323 pages. Another similar and commonly employed method is that of Chothia, published in Chothia, C., et al., *J. Mol. Biol.* (1987) 196: 901-917 and in Chothia, C., et al., *Nature* (1989) 342:877-883. An additional modification has been suggested by Abhinandan, K. R., et al., *Mol. Immunol.* (2008) 45:3832-3839. The present invention includes the CDR regions as defined by any of these systems or other recognized systems known in the art.

The specificities of the binding of the mAbs of the invention are defined, as noted, by the CDR regions mostly those of the heavy chain, but complemented by those of the light chain as well (the light chains being somewhat interchangeable). Therefore, the mAbs of the invention may contain the three CDR regions of a heavy chain and optionally the three CDR's of a light chain that matches it. Because binding affinity is also determined by the manner in which the CDR's are arranged on a framework, the mAbs of the invention may contain complete variable regions of the heavy chain containing the three relevant CDR's as well as, optionally, the complete light chain variable region comprising the three CDR's associated with the light chain complementing the heavy chain in question. This is true with respect to the mAbs that are immunospecific for a single epitope as well as for bispecific antibodies or binding moieties that are able to bind two separate epitopes.

Bispecific binding moieties may be formed by covalently linking two different binding moieties with different specificities. Multiple technologies now exist for making a single antibody-like molecule that incorporates antigen specificity domains from two separate antibodies (bi-specific antibody). Suitable technologies have been described by MacroGenics (Rockville, Md.), Micromet (Bethesda, Md.) and Merrimac (Cambridge, Mass.). (See, e.g., Orcutt, K. D., et al., *Protein Eng. Des. Sel.* (2010) 23:221-228; Fitzgerald, J., et al., *MAbs*. (2011) 1:3; Baeuerle, P. A., et al., *Cancer Res.* (2009) 69:4941-4944). For example, the CDR regions of the heavy and optionally light chain derived from one monospecific mAb may be coupled through any suitable linking means to peptides comprising the CDR regions of the heavy chain sequence and optionally light chain of a second mAb. If the linkage is through an amino acid sequence, the bispecific binding moieties can be produced recombinantly and the nucleic acid encoding the entire bispecific entity expressed recombinantly. As was the case for the binding moieties with a single specificity, the invention also includes the possibility of binding moieties that bind to one or both of the same epitopes as the bispecific antibody or binding entity/binding moiety that actually contains the CDR regions. The invention further includes bispecific constructs which comprise the complete heavy and light chain sequences or the complete heavy chain sequence and at least the CDR's of the light chains or the CDR's of the heavy chains and the complete sequence of the light chains.

The mAbs that are the subject of the present invention are not isolated from human blood or plasma, but rather are recombinantly produced. In brief, human blood cells that secrete antibodies are assessed to identify those cells that secrete mAbs of appropriate specificity and affinity. The RNA or DNA encoding these antibodies is extracted from the cells thus identified and the variable regions cloned. The resulting DNA encoding the heavy and light chain variable regions is coupled to DNA encoding generic constant regions and the resulting recombinant DNA encoding the complete antibody in each case is provided with control sequences to effect expression and secretion of the recombinant mAbs. Alternatively, the variable regions may be directly employed to encode, for example, single-chain forms of the mAbs. Suitable control sequences and secretion signal encoding sequences are well known in the art as are methods for recombinant production of encoding nucleic acids.

The mAbs of the invention are thus recombinantly produced using known techniques. The invention also includes nucleic acid molecules comprising nucleotide sequence encoding them, as well as vectors or expression systems that comprise these nucleotide sequences, cells containing expression systems or vectors for expression of these nucleotide sequences and methods to produce the binding moieties by culturing these cells and recovering the binding moieties produced. Any type of cell typically used in recombinant methods can be employed including prokaryotes, yeast, mammalian cells, insect cells and plant cells. Also included are human cells (e.g., muscle cells or lymphocytes) transformed with one or more recombinant molecules that encodes the novel antibodies.

Typically, expression systems for the mAbs of the invention include one or more nucleic acids encoding said at least the variable regions coupled to control sequences for expression. In many embodiments, the control sequences are heterologous to the nucleic acid encoding the protein. The invention is also directed to nucleic acids encoding the bispecific moieties and to recombinant methods for their production, as described above.

Thus, typically the nucleic acids encoding the mAbs or antigen-binding portions thereof are comprised in vectors that include expression systems for said encoding nucleic acids, which vectors are functional in transforming recombinant host cells for the production of the desired mAb or antigen-binding portion.

The invention is also directed to pharmaceutical and veterinary compositions which comprise as active ingredients the antibodies of the invention. The compositions contain suitable physiologically compatible excipients such as buffers and other simple excipients. The compositions may include additional active ingredients as well, in particular anti-tumor chemotherapeutic agents. The binding moieties of the invention may also be used in diagnosis.

The following examples are offered to illustrate but not to limit the invention.

Example 1

Human blood from anonymized donors from the Stanford Blood Center, obtained under informed consent, were screened for six ICM targets, including TIM-3 and B7-H3. The cells were subjected to the CellSpot™ assay to determine their ability to bind the antigens. The CellSpot™ assay is described in U.S. Pat. Nos. 7,413,868 and 7,939,344. After isolating Human peripheral blood mononuclear cells (PBMC's), they were stimulated with cytokines and mitogens to initiate a brief period of memory B cell proliferation, differentiation and antibody secretion (lasting 5 days) and plated for subjection to the assay. The encoding nucleic acids for the variable regions of positive antibodies were extracted and used to produce the antibodies recombinantly by cloning the DNA in expression vectors containing a signal peptide as well as the constant region for the heavy and light chains.

Example 2

The TIM-3 antibody molecules of the present invention were cloned following a survey of 22 blood donors for binding to 6 different ICM antigens, including the extracellular domain (ECD) of TIM-3. Anti-TIM-3 antibodies were detected in 15 of the donors at different frequencies (Table 1 and 2). BSA was used as a counterscreen to eliminate polyreactive antibodies. Four mAbs were cloned.

TABLE 1

Frequencies of anti-TIM-3 CellSpot ™'s in all doors tested

| Donor | TIM-3 # CellSpot ™'s/100K Memory Cells |
|---|---|
| SBC207 | 0.3 |
| SBC210 | 0.2 |
| SBC222 | 0 |
| SBC223 | 2.7 |
| SBC224 | 0 |
| SBC230 | 0.6 |
| SBC235 | 1.2 |
| SBC236 | 0.4 |
| SBC238 | 2.8 |
| SBC240 | 1.6 |
| SBC241 | 0 |
| SBC243 | 0 |
| SBC246 | 0.3 |
| SBC248 | 0.6 |
| SBC251 | 0 |
| SBC252 | 0 |
| SBC254 | 0.1 |
| SBC255 | 0.4 |
| SBC256 | 0 |
| SBC258 | 1.4 |
| INF 6.11 | 0.6 |
| INF 4.2 | 1.9 |

TABLE 2

Donors for Trellis Anti-TIM-3 antibodies

| TIM-3 TRLmAb | Donor # |
|---|---|
| 6042 | 236 |
| 6061 | 207 |
| 6099 | 254 |
| 6120 | 238 |

Purified mAbs were tested in adsorption ELISA using TIM-3 ECD, generated by Trellis in mammalian cells. Serial dilutions allowed calculating an estimate of the binding affinities (values listed in Table 3 are expressed as nM). TRL6061 and 6099 are of particular interest based on its sub-nM affinity to the target. A diverse set of germline variable regions was found in this group of mAbs as seen in Table 4.

TABLE 3

Affinities for Trellis Anti-TIM-3

| TIM-3 TRLmAb | Affinity (nM) |
|---|---|
| 6042 | 5 |
| 6061 | 0.005 |
| 6099 | 0.011 |
| 6120 | 28 |

TABLE 4

Germlines for Trellis Anti-TIM-3 antibodies

| TIM-3 TRLmAb | VH germline | VL germline |
|---|---|---|
| 6042 | IGHV5-51*01 | IGKV1-9*01 |
| 6061 | IGHV3-33*01 | IGLV3-10*01 |
| 6099 | IGHV3-38*01 | IGLV1-44*01 |
| 6120 | IGHV3-33*01 | IGLV3-10*01 |

Sequences of Trellis anti TIM-3 VH and VL in amino acids:

TRL6042 VH
(SEQ ID NO: 1)
qvqlvesgaevkkpgeslkiscegsgykftsywigwvrqmpgrgpewmgl iypsdsdtryspsfrgqvtisvdktistaylqwsslktsdtaiyycarll latectsdscfgdafdiwgqgtmvtvss TRL6042 VL (kappa)
(SEQ ID NO: 2)
divltqsptflsasvgdrvtitcrasqgissylawyqqkpgkapkillya astlqsgvpsrfsgsrsgteffitisslqpedfasyycqqfhnypftfgg gtkveikr TRL6061 VH
(SEQ ID NO: 3)
qvqlvesgggvvqpgrslrlscaasgfmfststsamhwvrqtpgkglewlav iwhdgsekyyadsvkgrfsisrdnyrdtlylqmnnlrvedtaiyycrggd vyeiwgqgtmvavss TRL6061 VL (lambda)
(SEQ ID NO: 4)
ddimltqppsysyspgqtaritcsgdavakryvywyqqksgqapvlvmye dnkrpsgiperfsgsssgtkatltitgalvedeadyycystdssgnlgaf gggskltvl TRL6099 VH
(SEQ ID NO: 5)
qvqlvesgaevkkpgasvkvsckafnytftsygiswvrqtpehglewmgw itnsnsnsaqkfqgrvsmttdtststaymqlrslssddtavyycariyid ynnygldvwgqgttvtvss TRL6099 VL (lambda)
(SEQ ID NO: 6)
divltqspsasgtpgqrviiscsgsssniggntvnwyqqlpgtapklliy sndqrpsgvpdrfsgsksgtsaslaisglqsedeadyycaawddslsgpa fgggtkltvlg TRL6120 VH
(SEQ ID NO: 7)
qvqlvesgggvvqpgrslrlscvasgfifrtyamhwvrqapgkglewvav iwpdgseryysdskgrftvsrdnskntlflqmnslrvddtamyycfargy sdsdyadhwgrgtrvtvss TRL6120 VL (lambda)
(SEQ ID NO: 8)
divmtqspsysyspgqtaritcsgdalstkfaywyqqksgqapvliyed nkrpsgiperfsgsgsgtmatlsyseaqvedeadyycfssdssgnlfmfg ggtkltvl Example 3

The B7-H3 antibody of the present invention was cloned following a survey of 14 blood donors for binding to 6 different ICM antigens, including the ECD of B7-H3. Anti-B7-H3 antibodies were detected in only 3 of the donors at low frequencies (Tables 5 and 6), suggesting that these antibodies are rarer than anti-TIM-3 antibodies in healthy donors (Table 1). BSA was used as a counterscreen to eliminate polyreactive antibodies. One antibody was cloned.

TABLE 5

Frequencies of anti-B7-H3 CellSpots in all doors tested

| Donor | B7-H3 # CellSpot ™'s/100K Memory Cells |
|---|---|
| SBC224 | 0 |
| SBC227 | 0 |
| SBC232 | 0 |
| SBC234 | 0.8 |
| SBC235 | 0.3 |
| SBC237 | 0 |
| SBC238 | 0 |
| SBC238 | 0.5 |
| SBC243 | 0 |
| SBC247 | 0 |
| SBC254 | 0 |
| SBC255 | 0 |
| AC1628 | 0 |
| AC1681 | 0 |

TABLE 6

Donors for Trellis Anti-B7-H3 antibody

| TIM-3 TRLmAb | Donor # |
|---|---|
| 4542 | 254 |

Purified mAb was tested in adsorption ELISA using B7-H3 ECD, generated by Trellis in mammalian cells. Serial dilutions allowed calculating an estimate of the binding affinities (value listed in Table 7 is expressed as nM). In Table 8 is shown the germlines for the heavy and light chain variable regions.

TABLE 7

Affinities for Trellis Anti-B7-H3 antibody

| B7-H3 TRLmAb | Donor # |
|---|---|
| 4542 | 5 |

TABLE 8

Germlines for Trellis Anti-B7-H3 antibody

| B7-H3 TRLmAb | VH germline | VL germline |
|---|---|---|
| 4542 | IGHV3-15*01 | IGKV4-1*01 |

Sequences of Trellis Anti-B7-H3 VH and VL in amino acids:

TRL4542 VH
(SEQ ID NO: 9)
qvqlvesggdlvqpgeslrlscaasgfifsdawmvwvrqapgkglewvg riktngdggttdltepvkgrftisrddsknmvylqmnnlrtedtaiyyc ttapgfwgqgtlvtvss TRL4542 VL (kappa)
(SEQ ID NO: 10)
diemtqspdslayslgeratinccksshnllyksnnknylawsqqkpgqp prlliywastrdsgvpdrfsgsgsgtdftltisslqaedvavyychqyy gtkwtfgqgtrveikr

The invention claimed is:

1. A monoclonal antibody (mAb) or effective antigen binding portion thereof, wherein said mAb or portion binds an extracellular portion of the immune checkpoint modulator (ICM) protein TIM-3, said mAb comprising:
   (a) the CDRs of the heavy chain variable region of TRL6042 (SEQ ID NO: 1) and the CDRs of the light chain variable region of TRL6042 (SEQ ID NO: 2);
   (b) the CDRs of the heavy chain variable region of TRL6061 (SEQ ID NO: 3) and the CDRs of the light chain variable region of TRL6061 (SEQ ID NO: 4);
   (c) the CDRs of the heavy chain variable region of TRL6099 (SEQ ID NO: 5) and the CDRs of the light chain variable region of TRL6099 (SEQ ID NO: 6); or
   (d) the CDRs of the heavy chain variable region of TRL6120 (SEQ ID NO: 7) and the CDRs of the light chain variable region of TRL6120 (SEQ ID NO: 8).

2. The mAb of claim 1, wherein said portion is an Fab fragment, an Fab' fragment, an Fab'-SH fragment, an F(ab')2 fragment, an Fv antibody, or wherein said mAb is a bispecific or multispecific antibody, a chimeric antibody, speciesized antibody or a complete antibody, including those comprising generic constant regions heterologous to variable regions.

3. A pharmaceutical composition comprising the mAb or portion of claim 1.

4. The mAb or portion of claim 1 for use in for treatment of patients with cancer, or for diagnostic detection of cancer or for treatment of immune system disorders.

5. A monoclonal antibody (mAb) or effective antigen binding portion thereof, wherein said mAb or portion has affinity for the immune checkpoint modulator (ICM) protein B7-H3, said mAb comprising the or effective antigen-binding portion thereof, which includes the CDRs of the heavy chain variable region of TRL4542 (SEQ ID NO: 9) and the CDRs of the light chain variable region of TRL 4542 (SEQ ID NO: 10).

6. The mAb of claim 5, wherein said portion is an Fab fragment, an Fab' fragment, an Fab'-SH fragment, an F(ab')2 fragment, an Fv antibody, or wherein said mAb is a bispecific or multispecific antibody, a chimeric antibody, speciesized antibody or a complete antibody, including those comprising generic constant regions heterologous to variable regions.

7. A pharmaceutical composition comprising the mAb or portion of claim 5.

8. The mAb or portion of claim 5 for use in for treatment of patients with cancer, or for diagnostic detection of cancer or for treatment of immune system disorders.

* * * * *

SEQUENCE LISTING

<160> NUMBER OF SEQ ID NOS: 10

<210> SEQ ID NO 1
<211> LENGTH: 128
<212> TYPE: PRT
<213> ORGANISM: Homo sapiens

<400> SEQUENCE: 1

```
Gln Val Gln Leu Val Glu Ser Gly Ala Glu Val Lys Lys Pro Gly Glu
1               5                   10                  15

Ser Leu Lys Ile Ser Cys Glu Gly Ser Gly Tyr Lys Phe Thr Ser Tyr
            20                  25                  30

Trp Ile Gly Trp Val Arg Gln Met Pro Gly Arg Gly Pro Glu Trp Met
        35                  40                  45

Gly Leu Ile Tyr Pro Ser Asp Ser Asp Thr Arg Tyr Ser Pro Ser Phe
    50                  55                  60

Arg Gly Gln Val Thr Ile Ser Val Asp Lys Thr Ile Ser Thr Ala Tyr
65                  70                  75                  80

Leu Gln Trp Ser Ser Leu Lys Thr Ser Asp Thr Ala Ile Tyr Tyr Cys
                85                  90                  95

Ala Arg Leu Leu Leu Ala Thr Glu Cys Thr Ser Asp Ser Cys Phe Gly
            100                 105                 110

Asp Ala Phe Asp Ile Trp Gly Gln Gly Thr Met Val Thr Val Ser Ser
        115                 120                 125
```

-continued

```
<210> SEQ ID NO 2
<211> LENGTH: 108
<212> TYPE: PRT
<213> ORGANISM: Homo sapiens

<400> SEQUENCE: 2

Asp Ile Val Leu Thr Gln Ser Pro Thr Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Leu
        35                  40                  45

Tyr Ala Ala Ser Thr Leu Gln Ser Gly Val Pro Ser Arg Phe Ser Gly
50                  55                  60

Ser Arg Ser Gly Thr Glu Phe Thr Leu Thr Ile Ser Ser Leu Gln Pro
65                  70                  75                  80

Glu Asp Phe Ala Ser Tyr Tyr Cys Gln Gln Phe His Asn Tyr Pro Phe
                85                  90                  95

Thr Phe Gly Gly Gly Thr Lys Val Glu Ile Lys Arg
            100                 105

<210> SEQ ID NO 3
<211> LENGTH: 115
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Met Phe Ser Thr Ser
            20                  25                  30

Ala Met His Trp Val Arg Gln Thr Pro Gly Lys Gly Leu Glu Trp Leu
        35                  40                  45

Ala Val Ile Trp His Asp Gly Ser Glu Lys Tyr Tyr Ala Asp Ser Val
50                  55                  60

Lys Gly Arg Phe Ser Ile Ser Arg Asp Asn Tyr Arg Asp Thr Leu Tyr
65                  70                  75                  80

Leu Gln Met Asn Asn Leu Arg Val Glu Asp Thr Ala Ile Tyr Tyr Cys
                85                  90                  95

Arg Gly Gly Asp Val Tyr Glu Ile Trp Gly Gln Gly Thr Met Val Ala
            100                 105                 110

Val Ser Ser
        115

<210> SEQ ID NO 4
<211> LENGTH: 109
<212> TYPE: PRT
<213> ORGANISM: Homo sapiens

<400> SEQUENCE: 4

Asp Asp Ile Met Leu Thr Gln Pro Pro Ser Val Ser Val Ser Pro Gly
1               5                   10                  15

Gln Thr Ala Arg Ile Thr Cys Ser Gly Asp Ala Val Ala Lys Arg Tyr
            20                  25                  30

Val Tyr Trp Tyr Gln Gln Lys Ser Gly Gln Ala Pro Val Leu Val Met
        35                  40                  45

Tyr Glu Asp Asn Lys Arg Pro Ser Gly Ile Pro Glu Arg Phe Ser Gly
50                  55                  60
```

Ser Ser Ser Gly Thr Lys Ala Thr Leu Thr Ile Thr Gly Ala Leu Val
65                  70                  75                  80

Glu Asp Glu Ala Asp Tyr Tyr Cys Tyr Ser Thr Asp Ser Ser Gly Asn
                85                  90                  95

Leu Gly Ala Phe Gly Gly Gly Ser Lys Leu Thr Val Leu
            100                 105

<210> SEQ ID NO 5
<211> LENGTH: 119
<212> TYPE: PRT
<213> ORGANISM: Homo sapiens

<400> SEQUENCE: 5

Gln Val Gln Leu Val Glu Ser Gly Ala Glu Val Lys Lys Pro Gly Ala
1               5                   10                  15

Ser Val Lys Val Ser Cys Lys Ala Phe Asn Tyr Thr Phe Thr Ser Tyr
                20                  25                  30

Gly Ile Ser Trp Val Arg Gln Thr Pro Glu His Gly Leu Glu Trp Met
            35                  40                  45

Gly Trp Ile Thr Asn Ser Asn Ser Asn Ser Ala Gln Lys Phe Gln Gly
        50                  55                  60

Arg Val Ser Met Thr Thr Asp Thr Ser Thr Ser Thr Ala Tyr Met Gln
65                  70                  75                  80

Leu Arg Ser Leu Ser Ser Asp Asp Thr Ala Val Tyr Tyr Cys Ala Arg
                85                  90                  95

Ile Tyr Ile Asp Tyr Asn Asn Tyr Gly Leu Asp Val Trp Gly Gln Gly
            100                 105                 110

Thr Thr Val Thr Val Ser Ser
        115

<210> SEQ ID NO 6
<211> LENGTH: 111
<212> TYPE: PRT
<213> ORGANISM: Homo sapiens

<400> SEQUENCE: 6

Asp Ile Val Leu Thr Gln Ser Pro Ser Ala Ser Gly Thr Pro Gly Gln
1               5                   10                  15

Arg Val Ile Ile Ser Cys Ser Gly Ser Ser Ser Asn Ile Gly Gly Asn
                20                  25                  30

Thr Val Asn Trp Tyr Gln Gln Leu Pro Gly Thr Ala Pro Lys Leu Leu
            35                  40                  45

Ile Tyr Ser Asn Asp Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Gly Pro Ala Phe Gly Gly Gly Thr Lys Leu Thr Val Leu Gly
            100                 105                 110

<210> SEQ ID NO 7
<211> LENGTH: 120
<212> TYPE: PRT
<213> ORGANISM: Homo sapiens

<400> SEQUENCE: 7

-continued

Gln Val Gln Leu Val Glu Ser Gly Gly Val Val Pro Gly Arg
1               5                   10                  15

Ser Leu Arg Leu Ser Cys Val Ala Ser Gly Phe Ile Phe Arg Thr Tyr
            20                  25                  30

Ala Met His Trp Val Arg Gln Ala Pro Gly Lys Gly Leu Glu Trp Val
        35                  40                  45

Ala Val Ile Trp Pro Asp Gly Ser Glu Arg Tyr Tyr Ser Asp Ser Thr
    50                  55                  60

Lys Gly Arg Phe Thr Val Ser Arg Asp Asn Lys Asn Thr Leu Phe
65                  70                  75                  80

Leu Gln Met Asn Ser Leu Arg Val Asp Thr Ala Met Tyr Tyr Cys
                85                  90                  95

Phe Ala Arg Gly Tyr Ser Asp Ser Asp Tyr Ala Asp His Trp Gly Arg
                100                 105                 110

Gly Thr Arg Val Thr Val Ser Ser
            115                 120

<210> SEQ ID NO 8
<211> LENGTH: 108
<212> TYPE: PRT
<213> ORGANISM: Homo sapiens

<400> SEQUENCE: 8

Asp Ile Val Met Thr Gln Ser Pro Ser Val Ser Val Ser Pro Gly Gln
1               5                   10                  15

Thr Ala Arg Ile Thr Cys Ser Gly Asp Ala Leu Ser Thr Lys Phe Ala
            20                  25                  30

Tyr Trp Tyr Gln Gln Lys Ser Gly Gln Ala Pro Val Leu Val Ile Tyr
        35                  40                  45

Glu Asp Asn Lys Arg Pro Ser Gly Ile Pro Glu Arg Phe Ser Gly Ser
    50                  55                  60

Gly Ser Gly Thr Met Ala Thr Leu Ser Val Ser Glu Ala Gln Val Glu
65                  70                  75                  80

Asp Glu Ala Asp Tyr Tyr Cys Phe Ser Asp Ser Ser Gly Asn Leu
                85                  90                  95

Phe Met Phe Gly Gly Gly Thr Lys Leu Thr Val Leu
                100                 105

<210> SEQ ID NO 9
<211> LENGTH: 115
<212> TYPE: PRT
<213> ORGANISM: Homo sapiens

<400> SEQUENCE: 9

Gln Val Gln Leu Val Glu Ser Gly Gly Asp Leu Val Gln Pro Gly Glu
1               5                   10                  15

Ser Leu Arg Leu Ser Cys Ala Ala Ser Gly Phe Ile Phe Ser Asp Ala
            20                  25                  30

Trp Met Val Trp Val Arg Gln Ala Pro Gly Lys Gly Leu Glu Trp Val
        35                  40                  45

Gly Arg Ile Lys Thr Asn Gly Asp Gly Thr Thr Asp Leu Thr Glu
    50                  55                  60

Pro Val Lys Gly Arg Phe Thr Ile Ser Arg Asp Asp Ser Lys Asn Met
65                  70                  75                  80

Val Tyr Leu Gln Met Asn Asn Leu Arg Thr Glu Asp Thr Ala Ile Tyr
                85                  90                  95

```
Tyr Cys Thr Thr Ala Pro Gly Phe Trp Gly Gln Gly Thr Leu Val Thr
            100                 105                 110

Val Ser Ser
        115

<210> SEQ ID NO 10
<211> LENGTH: 114
<212> TYPE: PRT
<213> ORGANISM: Homo sapiens

<400> SEQUENCE: 10

Asp Ile Glu Met Thr Gln Ser Pro Asp Ser Leu Ala Val Ser Leu Gly
1               5                   10                  15

Glu Arg Ala Thr Ile Asn Cys Lys Ser Ser His Asn Leu Leu Tyr Lys
            20                  25                  30

Ser Asn Asn Lys Asn Tyr Leu Ala Trp Ser Gln Gln Lys Pro Gly Gln
        35                  40                  45

Pro Pro Arg Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Gly Thr Lys Trp Thr Phe Gly Gln Gly Thr Arg Val Glu Ile
            100                 105                 110

Lys Arg
```